United States Patent
Schwarze et al.

(10) Patent No.: US 7,610,079 B2
(45) Date of Patent: Oct. 27, 2009

(54) SHOCK WAVE IMAGING SYSTEM

(75) Inventors: Werner Schwarze, Jena (DE); Hugo Stephan, Jena (DE)

(73) Assignee: AST GmbH, Jena (DE)

( * ) Notice: Subject to any disclaimer, the term of this patent is extended or adjusted under 35 U.S.C. 154(b) by 0 days.

(21) Appl. No.: 11/459,664

(22) Filed: Jul. 25, 2006

(65) Prior Publication Data
US 2008/0033287 A1   Feb. 7, 2008

(51) Int. Cl.
A61B 5/05    (2006.01)
A61B 8/00    (2006.01)
A61H 1/00    (2006.01)

(52) U.S. Cl. .............. 600/427; 600/439; 601/4
(58) Field of Classification Search ......... 600/427, 600/439; 601/2–4; 378/62
See application file for complete search history.

(56) References Cited

U.S. PATENT DOCUMENTS

| | | | |
|---|---|---|---|
| 4,276,779 A | 7/1981 | Davis, Jr. | |
| 4,537,074 A | 8/1985 | Dietz et al. | |
| 4,539,989 A | 9/1985 | Forssmann et al. | |
| 4,807,627 A | 2/1989 | Eisenmenger | |
| 4,984,575 A * | 1/1991 | Uchiyama et al. | 600/439 |
| 5,119,801 A | 6/1992 | Eizenhoefer et al. | |
| 5,174,280 A | 12/1992 | Gruenwald et al. | |
| 5,222,484 A | 6/1993 | Krauss et al. | |
| 5,287,856 A | 2/1994 | Treiber | |
| 5,301,660 A | 4/1994 | Rattner | |
| 5,350,351 A | 9/1994 | Saffer | |
| 5,419,327 A | 5/1995 | Rohwedder et al. | |
| 5,419,335 A | 5/1995 | Hartmann et al. | |
| 5,545,124 A | 8/1996 | Krause et al. | |
| 5,595,178 A | 1/1997 | Voss et al. | |
| 5,921,930 A | 7/1999 | Uberle | |
| 6,128,575 A * | 10/2000 | Croom et al. | 701/226 |
| 6,306,089 B1 * | 10/2001 | Coleman et al. | 600/437 |
| 2001/0023326 A1 | 9/2001 | Spector | |
| 2001/0039379 A1 | 11/2001 | Hagelauer | |
| 2003/0174809 A1 | 9/2003 | Neumann | |
| 2005/0010140 A1 | 1/2005 | Forssmann | |

FOREIGN PATENT DOCUMENTS

| | | |
|---|---|---|
| DE | 40 30 408 A1 | 8/1991 |
| DE | 10065450 | 7/2002 |
| DE | 102005017724 | 11/2006 |
| EP | 1445758 | 8/2004 |

OTHER PUBLICATIONS

European Search Report dated Jul. 17, 2009, Application No. EP 07 01 4387.0, 6-pgs.

* cited by examiner

Primary Examiner—Eric F Winakur
Assistant Examiner—Michael T Rozanski
(74) Attorney, Agent, or Firm—King & Spalding LLP (57) ABSTRACT

A system or apparatus 2 for visually displaying and treating a treatment volume 100 located in a human or animal body 1 is disclosed wherein the treatment volume 100 is detected by a location finding imaging instrument 10 and displayed on a monitor 12 and a treatment instrument 20 is preferably oriented in response to the visual display to direct a treatment path 25 which is visually displayed superimposed onto the treatment volume 100.

31 Claims, 3 Drawing Sheets

SHOCK WAVE IMAGING SYSTEM

TECHNICAL FIELD

This invention relates to a new and improved system to image and position a shock wave unit for optimal performance during therapeutic shock wave treatments.

BACKGROUND OF THE INVENTION

Electro-hydraulic shock wave systems have been used to disintegrate kidney and urethral stones by applying focused shock waves to the stone. A few hundred up to a few thousand shock waves may be required to break a stone within a mammal into small pieces of 3-4 mm diameter which are able to pass over a period of several weeks through the urethra and the bladder out of the patient's body.

Devices using electro-hydraulic (U.S. Pat. No. 4,539,989), piezoceramic (U.S. Pat. No. 5,119,801) or electromagnetic (U.S. Pat. No. 5,174,280) shock wave or pressure pulse generating elements have been described.

The patents used herein to illustrate the invention and, in particular, to provide additional details respecting the practice are incorporated herein by reference in their entirety.

In certain of non-urological applications, shock waves and pressure pulses may be used to treat bone fracture, non-unions, or other orthopedic conditions. The treated indications may be related to tendons, ligaments, soft tissue and include muscle pain and calcification in tissue. Suitable devices and procedures have been described (U.S. Pat. No. 5,545,124 and U.S. Pat. No. 5,595,178).

Known devices generally make use of more or less strong focused shock waves which are focused by ellipsoidal reflectors in electro-hydraulic devices (U.S. Pat. No. 4,539,989) or by parabolic reflectors in devices using electromagnetic sources which are emitting waves from a cylindrical surface (U.S. Pat. No. 5,174,280). Other electromagnetic sources may make use of acoustic lenses of different shapes, for example, concave or convex, depending on the sound velocity and density of the lens material used (U.S. Pat. No. 5,419,335 and European Patent 1 445 758 A2). Piezoelectric sources often use spherical surfaces to emit acoustic pressure waves which are self focused to the center of the sphere (U.S. Pat. No. 5,222,484). The same type of focusing has been used in spherical electromagnetic devices (U.S. Pat. No. 4,807,627).

Since 1971 extracorporeal shock wave therapy (hereinafter ESWT) has been used successfully and with a low rate of adverse reactions in the field of urology. Despite the relatively high energy flow densities used during ESWT, no major complications (e.g. malignant degeneration of the treated tissue) have been reported.

The German urologist G. Haupt deserves the credit for the acceptance ESWT has gained in the fields of orthopaedics and traumatology as well. Urologists have noticed, that larger amounts of energy (i.e. a larger number of pulses) were required to disintegrate calculi in the urethra and bladder than to break down renal calculi. Initially neither the physicists nor the medical scientists involved in these studies had a plausible explanation for this discrepancy. It was while reviewing follow-up x-rays to detect any recurrences of calculi in patients treated for urethral or bladder stones in 1986 that Haupt first noted a thickening of the ala of the ileum, an anatomical structure lying directly in the path of the shock waves aimed at the calculi. This finding was significant since it indicated that a) bone absorbs shock waves and b) shock waves evidently also trigger biological reactions in bone. Haupt subsequently demonstrated the osteoinductive effect of focused shock waves in animal experiments.

Since it is mainly the physical properties of shock waves that play a central role in the use of extracorporeal shock wave therapy for urological applications, basic research on the use of shock waves for orthopedic and traumatological applications also focused primarily on these dynamic mechanical force related type properties.

This mechanistic model attempts to explain the effect of shock waves in tissue by postulating that the shock wave creates micro lesions in the tissue on which it is concentrated without, however, destroying the surrounding soft-tissue and thus triggers repair processes leading to healing.

This model of action was the reason, moreover, that Schaden et al used high numbers of pulses (i.e. up to 12,000 for treatment of the long bones) when employing shock waves for the first time to treat patients with pseudoarthrosis. Several of these treatments had to be terminated after only 3,000 to 4,000 pulses for technical reasons, however, it was noted that the treatment resulted in healing of the patients pseudoarthrosis despite (or perhaps because of) this circumstance. This observation was congruent with the results of the basic research carried out by M. Maier, who demonstrated that the optimal osteoinductive effect of shock waves on rat femora took place at energy flow densities and pulse numbers which caused practically no histological demonstrable tissue destruction. One consequence of this finding was that basic research on shock waves concentrated increasingly on the biological effects of shock waves.

C. J. Wang discovered that a variety of substances displaying high biological activity are released during and after the application of shock waves to tissue. The production of nitric oxygen (NO), vessel endothelial growth factor (VEGF), bone morphogenetic protein (BMP), and other growth factors have been demonstrated. Furthermore, Maier discovered a decline in the number of small-myelinized neurons after shock wave therapy, an observation that could explain the analgesic effect of shock wave therapy. As a consequence of these findings, the mechanistic model was increasingly relegated to a secondary role and supplanted by a microbiological model explaining the action of shock waves.

In practice the use of ESWT has been a results oriented science wherein a clear and accurate understanding of the actual healing process was neither understood nor fully appreciated. As a result a variety of treatments and uses of ESWT in mammals had heretofore never been tried or attempted or if tried, the outcomes were at best mixed.

A primary factor in the reluctance to use ESWT was that the believed threshold energy requirements were so high that the surrounding tissue would hemorrhage, exhibited by hematomas and bleeding around the treated site. This phenomenon is particularly known in the area of focused emitted waves designed for deep penetration into the patient. US patent publication 2005/0010140 recites the disadvantageous effects of cavitation phenomena can be controlled wherein the shock wave source is connected to a control means which controls the release frequency of shock waves as a function of pulse energy in such a manner that higher pulse energy correlates with lower release frequencies of the shock waves and vice versa. The avoidance of cavitation occurrences would it is postulated result in far less pain for the patient.

Up to the present, shock wave units focused acoustical energy on one point or focal point hence the name focused shock waves. More recent patents DE10065450 or DE registered no. 102205017724-22 respectively publications as Eisenmenger UMB 2002, 28369-774 have described shock wave units with a larger therapy volume. In particular these new units can provide effective wave transmission over volumes far greater than a focal point. In fact the volumetric region of effective wave energy transmission can be considerably larger and the projected profile of this therapeutic volume can be established to a reasonable degree of certainty.

In today's clinical routine, all positioning and real time monitoring systems connected to shock wave units are based on a targeting on one point, which represents the point of highest energy.

The clinician is requested to position the volume to be treated (for example the stone) onto this point. To do so, expensive technology by means of a maneuverable patient table or shock wave unit must be utilized.

Amongst experts it is well accepted, that the marked focal point represents not necessarily the point of the maximal energy. The reasons are that this theoretical point is only established by measurements in water. It is considered the best possible approximation, because the propagation of the shock waves through the human body is conjugated by the changing tissues as skin, muscle, fat, etc.

Further aging processes of some types of shock wave units as well as the selected energy level always causes a shift of the point of highest energy from a predicted theoretical point. The shift caused by a burning of the electrode means the theoretical point is constantly shifting after repeated transmission pulses. Those described systematic deviations are being enlarged by any controlled or uncontrolled movements of the patients, e.g. respiration.

For the application of new shock wave units with larger therapy volume as described above, a positioning device on one point becomes practically useless and even in the old focal point shock wave units the emitted energy profile created a gradient form of therapeutic energy that could be very useful to the clinician treating a bone fracture wherein the control of the emitted energy profile is represented in a therapeutic volume which is invaluable in shock wave treatments.

SUMMARY OF THE INVENTION

A system or apparatus for visually displaying and treating a treatment volume located in a human or animal body is disclosed wherein the treatment volume is detected by a location finding imaging instrument and displayed on a monitor and a treatment instrument is preferably oriented in response to the visual display to direct a treatment path which is visually displayed superimposed onto the treatment volume. The system or apparatus has a location finding imaging instrument; a shock wave treatment instrument; one or more control units for processing data or signals received from the location finding imaging instrument and the shock wave treatment instrument; an image display monitor receives data or signals from the one or more control units for displaying both the image of the treatment volume and displaying the treatment path as a projected shock wave energy profile set at a predetermined energy.

The system or apparatus preferably includes a means for positioning or orienting the location finding imaging instrument and a means for positioning or orienting the shock wave treatment instrument wherein changes in the treatment instrument orientation changes the direction of the treatment path and the corresponding shock wave energy profile which are displayed on the image display monitor.

The system or apparatus further includes a means to adjust the power, pulse or energy profile on the shock wave treatment instrument and these changes are reflected on the image display monitor as new shock wave energy profiles.

The location finding imaging instrument can include an ultrasound device, an x-ray device or radio wave image, device or any other image or scanning device, any of which can provide an image of the treatment volume, preferably a three dimensional image.

Eisenberger at all describes in J Urol 2003 Auf 170 (2 Pt 1):388-9 "The first clinical results of wide focus and low pressure EWSL" for those applications the described method of positioning carries big advantages.

The display of the shock wave treatment profile is superimposed on the treatment volume in such a way the clinician can adjust the energy profile in terms of orientation, power, pulse frequency, pulse amplitude or duration or any combination thereof, and a corresponding change will be reflected on the display monitor. The system can also display a simulated treatment if so desired prior to initiating actual treatment. The simulated treatment will display the actual therapeutic volume being displayed with a superimposed representation of the shock wave profile simultaneously displayed. In this way the clinician can readjust any of the treatment parameters prior to actually applying the treatment. Once an optimal treatment profile is established the clinician can activate the system and the treatment of the therapeutic volume can begin with a real time image display allowing possibly for a few seconds delay caused by the calculation, being transmitted. Assuming the treatment is directed at breaking or otherwise pulverizing a kidney stone, or other concrement, the transmitted shock waves can be terminated as soon as the desired results are achieved as seen on the monitor. The advantages of the system are the patient will receive a shock wave treatment that is satisfactorily certain of the desired results and is not over treated so as to avoid any unnecessary surrounding tissue hemorrhaging. The system insures a more efficient and therefore better use of such shock wave devices that can non-invasively provide the clinician with a real time prognosis of his patient's condition. The system preferably includes data storage and file saving capability such that the procedure can be saved as a documented file which will be invaluable to review in the event of a re-occurrence or to check subsequent healing.

BRIEF DESCRIPTION OF THE DRAWINGS

These and further objects of the present invention will be more fully understood from the following description of the invention reference to the illustrations appended hereto.

DETAILED DESCRIPTION OF THE INVENTION

Figure 1:
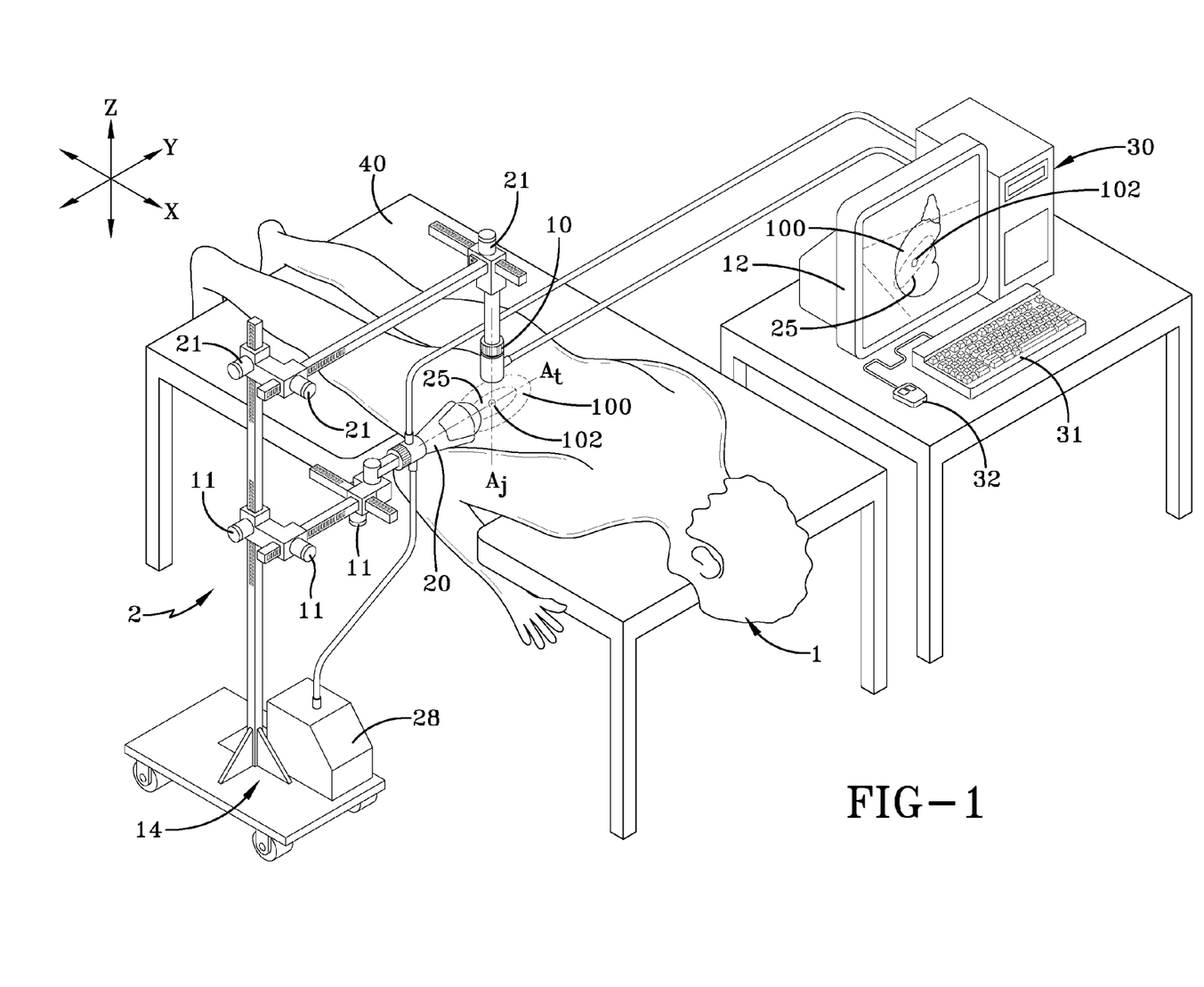
FIG. 1 is a perspective view of a patient on a table with the apparatus of the present invention.
Figure 2:
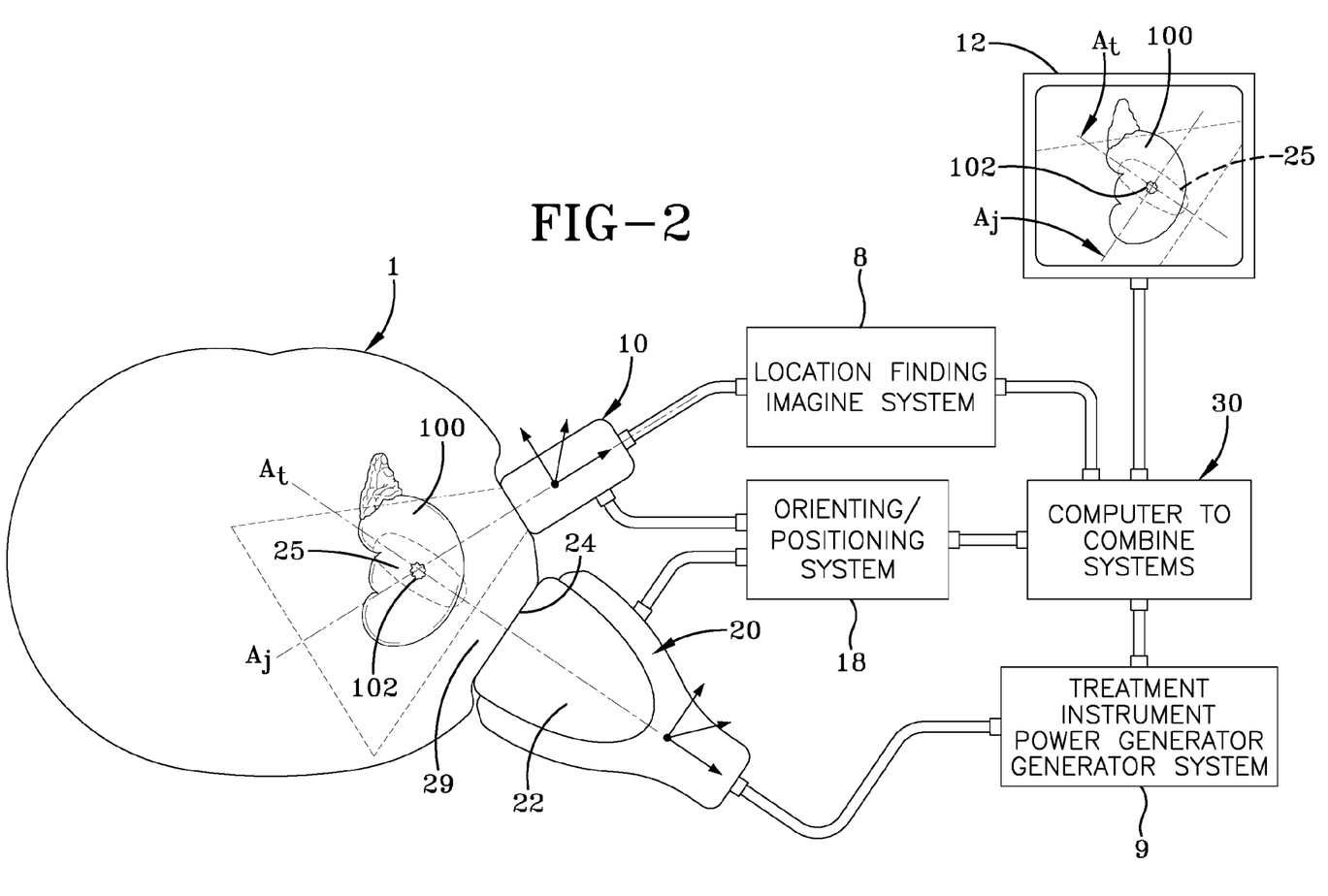
FIG. 2 is a plan schematic view of the device of the present invention being used on a portion of the patient showing the treatment volume.

With reference to FIG. 1 a patient 1 is shown lying face down on an operating table 40. As shown an exemplary apparatus 2 is positioned to one side of the patient 1 about midway along the torso. An imaging device 10 is shown attached to a portable stand 14 and directed downwardly aiming in a region of the patient's kidney 100. The imaging device 10 has a projected axis or orientation $A_i$, $A_i$ as illustrated being a vertical line. A treatment device 20 is shown oriented and has a treatment path 25 having a centerline directed along an axis $A_t$, as shown $A_t$ intersects the axis $A_i$ at location 102. Both devices are independently movable in the x,y,z axis either manually or an orienting/positioning system 18 by one or more servomotors 11, 21 such that the image device 10 can be oriented in any desired direction to achieve an optimal view of the treatment volume 100 on an image display monitor 12 while the treatment device 20 can have the path 25 directed in any desired orientation which is also displayed on the monitor 12. In this example the treatment volume 100 is the patient's kidney 100. In other procedures the treatment volume 100 can be any volume of tissue or bone mass wherein a treatment is to be viewed and treated, by way of example fractured bones, non unions or any part or whole portion of a body tissue or organ in need of treatment.

As shown the image device 10 which is a component of a location finding imaging system 8 can be an ultrasound device, an x-ray head or a radio image or scanning device or any other apparatus capable of projecting the treatment volume 100 onto the image display monitor 12. The image signal as generated is converted to an electronic data stream or electronic signal that is preferably fed into a control unit 30 such as a computer processor 30 that relays the signal to an image display monitor 12. Preferably the monitor 12 shows the treatment volume 100 in real time or a reasonably close approximation thereto. In this way the clinician can visually see the treatment volume 100 and can precisely observe the desired location to be treated. In the example the kidney 100 having a kidney stone 102 can be visually observed.

Once the image is set by the clinician, he or she can direct the treatment instrument 20 by importing the x, y, z coordinates of location 102 of the desired treatment volume 100 into the computer 30. This can be accomplished by simply moving a cursor shown on the monitor 12 onto the displayed area of interest and clicking the mouse 32 or entering the coordinates using the keyboard 31 so the position coordinates can be inputted back to the computer 30. The computer 30 can then direct the orientation of the treatment instrument 20 to orient the treatment head to point the treatment path 25 to the selected coordinates using the automated orienting positioning system 18. Since the treatment path 25 is a graphical representation of the shock wave transmission at a minimum energy level $P_e$ that is of a three dimensional shape the axis $A_t$ is centrally located within this volume of energy originating from the shock wave head 22 or lens 24 and extending outwardly. The axis $A_t$ therefore passes through the centroid C of the volume of projected energy. Accordingly the software can align the axis $A_t$ to intersect the selected coordinates desired location or more preferably will move the treatment path 25 such that the centroid C of the energy profile is moved directly onto the selected coordinates or desired location. Alternatively the clinician can manually orient the treatment instrument 20 and the instrument will send a location or orientation signal through the computer processor 30 back to the image display monitor 12 and a picture of the projected treatment path 25 which as shown in FIG. 1 in the example is the treatment path 25 which is centered about the axis $A_t$ and aligned with intersection of the axis $A_i$ and axis $A_t$ at location 102. The choice of the location for the treatment instrument 20 is totally at the clinician's discretion and therefore the axis $A_t$ can be directed offset from the selected axis $A_i$ or location 102 if so desired causing a shift in the treatment path 25 if so desired. In such a case the projected shift of the treatment path 25 would be shown on the display monitor superimposed on the treatment volume 100, but with the axis $A_t$ shifted relative to the location 102. This shifting makes it possible to avoid sensitive or inflamed tissue, but still strike the desired volume with a sufficient treatment dosage or energy to destroy the kidney stone 102.

The treatment instrument 20 is an acoustic shock wave device 20. The device as shown has a shock wave head 22 positioned against the patient's body 1 and preferably coupled acoustically by using a gel 29 between the patient's skin and the lens 24 of the shock wave head 22 to improve the transmission efficiency as is known in the art.

The shock wave head 22 is mounted on the portable stand 14 and is movable about the x, y, z coordinates manually or by one or more servomotors 21 of the orienting/positioning system 18 that are preferably controlled by the computer 30. As previously mentioned positioning of the projected treatment path 25 can be done manually as the clinician observes the monitor 12 or automatically by moving a cursor shown on the monitor 12 using the mouse 32 or keyboard 31 and clicking on a location wherein the clinician desires the treatment path 25 to be directed wherein the computer will direct the servomotors 21 to orient the shock wave head 22 so the path 25 has its centerline axis $A_t$ intersect the desired volume at the selected location, preferably by having the centroid C of the projected energy profile moved to the selected coordinates.

Once the images of the treatment path 25 and the treatment volume 100 are superimposed and visually displayed on the monitor, the clinician may desire to adjust the size of the treatment path 25.

Figure 3:
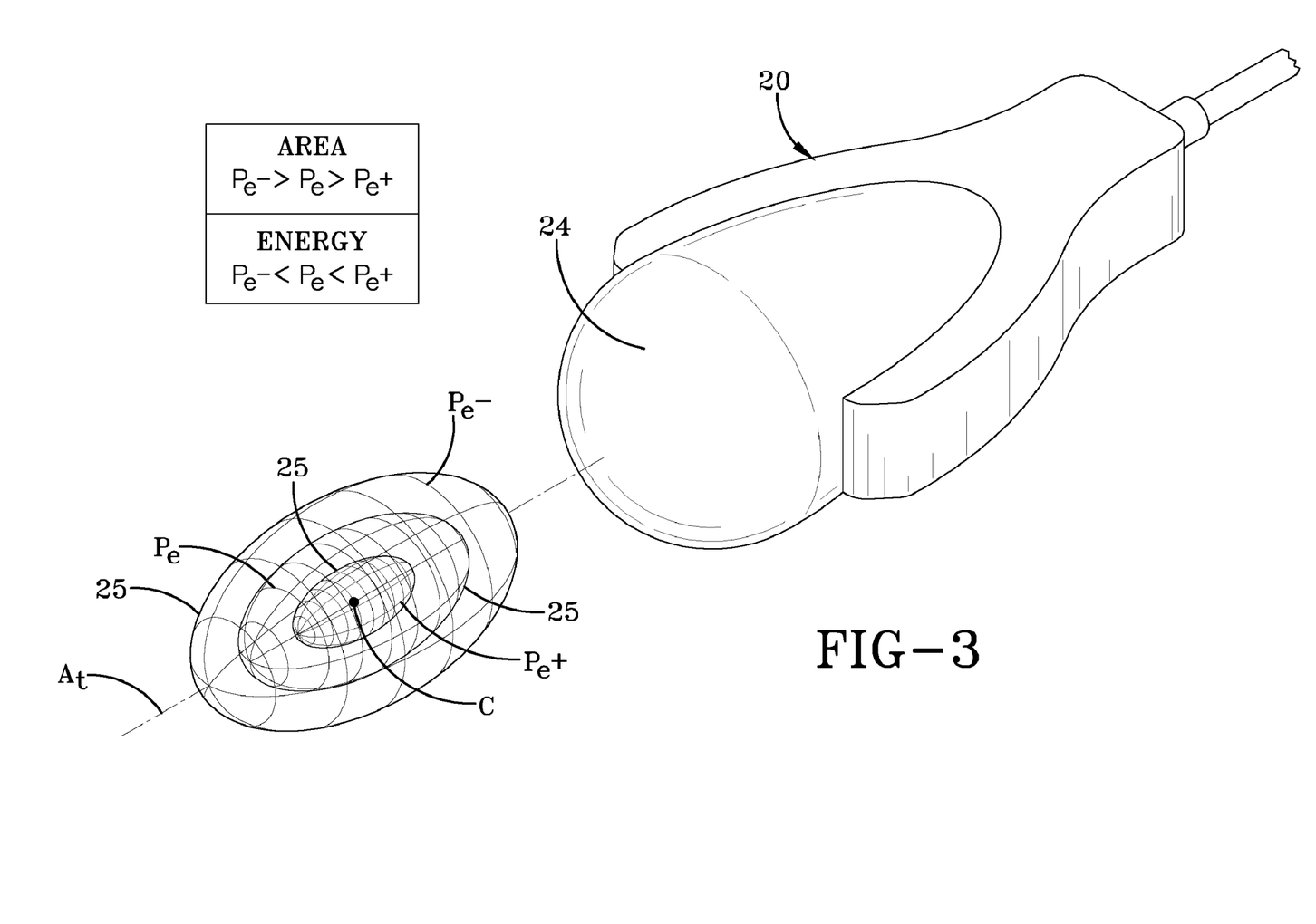
FIG. 3 is an exemplary view of the treatment instrument showing alternative power levels.

As used herein and shown as one exemplary treatment path 25 in FIG. 3 the treatment path 25 is the region wherein a threshold minimum energy level $P_e$ is predicted to be transmitted from the shock wave generator source 28 to the shock wave head 22. This minimum energy level $P_e$ changes with the parameters selected. In not all, but some shock wave generators the energy level $P_e$ can be adjusted upward creating a higher intensity $P_{e+}$ in a generally smaller displayed volume if desired or lowered to $P_{e-}$ creating a larger displayed volume by adjusting the settings on the power generator system 9 which controls the shock wave power generator source 28 as shown in the example of FIG. 3. In electromagnetic and piezo-systems the treatment path is becoming smaller with increasing energy, this is not necessarily the case for electro hydraulic units. The clinician by observing the display monitor can adjust shock wave amplitudes, power levels and pulse durations to create a very customized treatment dosage for each individual patient and each condition as the treatment area dictates. While the monitor display 12 of the treatment volume 100 may be in black and white it is preferred that the treatment path 25 and optionally its centerline axis $A_t$ be shown as an outlined wire mesh view of three dimensional shape with the straight line axis $A_t$ passing centrally through the path 25, all in a contrasting color so the clinician can observe the treatment volume image without obstructing the view due to the superimposed outline of the treatment path 25. As shown the treatment path 25 has an energy profile that covers an oblong ellipsoidal or elongated oval shape. Alternatively, this preferred three dimensional view can be shown as a cross sectional area lying in a single plane if so desired to give an even clearer view of the image of the treatment volume 100. The axis $A_i$ and $A_t$ alternatively need not be displayed at the option of the clinician.

Once a treatment dosage is selected it is possible to create a simulated treatment prior to actually treating. The simulated treatment allows the clinician to visually observe the treatment volume 100 and a pulsating superimposed treatment path 25 on the monitor 12 over the duration of the simulation.

Alternatively the clinician can initiate the selected treatment activating the shock wave transmission while observing the image of the treatment volume 100 displayed on the monitor 12 and in so doing can observe in real time or within fractions of seconds of real time observe the treatment and the reaction of the kidney stone 102 being treated. Accordingly the treatment can be stopped immediately upon pulverizing the stone 102 or can be interrupted if the treatment is not achieving a desired result. In the latter case the clinician can make orientation or power adjustments to the treatment instrument and then continue the process.

This combination of imaging a treatment volume and positioning the treatment instrument using a superimposed display of the treatment path and the treatment volume is a revolutionary concept that provides the potential to a high medical certainty that the observed treatment results are achieved in a most efficient manner.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A system for visually displaying and treating a location in a treatment volume in a human or animal body, the system comprising:
    a location finding imaging instrument that detects the treatment volume and the location to be treated within the treatment volume;
    a treatment instrument, the treatment instrument being oriented to direct energy along a treatment path in response to the display of the treatment volume and the location to be treated within the treatment volume;
    an image display monitor; and
    at least one control unit configured to control the image display monitor to display the detected treatment volume, the detected location to be treated within the treatment volume, and an energy level region of the treatment path, wherein the image display monitor displays the region of the treatment path as a graphical representation in at least two dimensions superimposed on the displayed treatment volume and the location to be treated within the treatment volume.

2. The system of claim 1, wherein the graphical representation of the region of the treatment path is visually displayed as an outline of a three dimensional shape.

3. The system of claim 1, wherein the graphical representation of the region of the treatment path is visually displayed as an outline of an area defined in a single plane.

4. The system of claim 1, wherein the treatment instrument is a shock wave instrument, and wherein region of the treatment path is a projected shock wave energy profile set at a predetermined energy.

5. The system of claim 4, wherein the at least one control unit processes data or signals received from the location finding instrument and the shock wave instrument and communicates the data or signals to the image display monitor, and
    wherein the image display monitor receives the data or signals from the at least one control unit to display the treatment volume, the location to be treated within the treatment volume, and the region of the treatment path.

6. The system of claim 5, further comprising:
    means for orienting the location finding imaging instrument; and
    means for orienting the shock wave instrument,
    wherein changes in the treatment instrument orientation change the direction of the region of the treatment path that is displayed on the image display monitor.

7. The system of claim 6, wherein the means for orienting the shock wave instrument comprises a shock wave generator connected to the at least one control unit.

8. The system of claim 6, wherein the means for orienting the shock wave instrument comprises at least one servomotor movably controlled by the at least one control unit.

9. The system of claim 6, wherein the means for orienting the treatment instrument is configured to:
    identify a position of the treatment location within the treatment volume image displayed on the image display monitor; and
    receive coordinates to direct movement of the treatment instrument to align at least one of an axis of the treatment path and a centroid of the region of the treatment path onto the received coordinates.

10. The system of claims 5, further comprising:
    means to adjust at least one parameter of power, pulse frequency, pulse amplitude, and duration, thereby adjusting the energy profile of the shock wave instrument,
    wherein the adjustments are reflected on the image display monitor as changes in a size or shape of the region of the treatment path based on the adjusted parameters.

11. The system of claim 1, wherein the at least one control unit comprises a computer.

12. The system of claim 11, wherein the location finding imaging instrument comprises one of an ultrasound device, an x-ray device, and a radio wave image device.

13. The system of claim 1, further comprising a processor that simulates an activation of the treatment instrument, wherein the processor displays the simulation on the image display monitor as the region of the treatment path.

14. The system of claim 1, wherein a location of the region of the treatment path is adjusted on the image display monitor with respect to the displayed treatment volume and the displayed location to be treated within the treatment volume based on an adjustment to an orientation of the treatment instrument.

15. The system of claim 1, further comprising a storage component for storing attributes of a treatment of the treatment location, wherein the attributes comprise at least one of a volume of the region of the treatment path, an area of the region of the treatment path, an orientation of the region of the treatment path, a power of the region of the treatment path, a pulse frequency of the region of the treatment path, a pulse amplitude of the region of the treatment path, a duration of the treatment, the treatment volume, and an identity of the human or animal body.

16. The method of claim 1, wherein the location finding imaging instrument and the treatment instrument are movable independently from one another in three dimensions.

17. The system of claim 1, wherein the region of the treatment path visually displayed on the image display monitor comprises a threshold minimum energy level, the threshold minimum energy level being based on one or more parameters.

18. A system for visually displaying and treating a location in a treatment volume in a human or animal body, the system comprising:
    a location finding imaging instrument configured to detect the treatment volume and the location to be treated within the treatment volume;

a treatment instrument configured to direct enemy along a treatment path on the location to be treated in the treatment volume;

an image display device; and at least one control unit configured to control the image display device to display the detected treatment volume, the detected location to be treated within the treatment volume, and an enemy level region of the treatment path, wherein the image display device displays the region of the treatment path as a three-dimensional volumetric shape superimposed on the displayed treatment volume and location to be treated within the treatment volume.

19. The system of claim 18, wherein the treatment instrument is a shock wave instrument, and wherein the region of the treatment path is a projected shock wave energy profile set at a predetermined energy.

20. The system of claim 18, further comprising a processor configured to simulate activation of the treatment instrument to determine a simulated treatment path prior to activation of the treatment instrument, wherein the image display device displays a simulated region of the treatment path as the three-dimensional volumetric shape superimposed on the treatment volume and the location to be treated within the treatment volume.

21. The system of claim 18, wherein the at least one control unit is configured to process information received from the location finding instrument and the treatment instrument and to communicate signals based on the received information to the image display device, and wherein the image display device displays the treatment volume, the location to be treated within the treatment volume, and the region of the treatment path based on the signals received from the at least one control unit.

22. The system of claim 21, further comprising:

means for orienting the location finding imaging instrument; and means for orienting the treatment instrument in response to location to be treated within the treatment volume displayed on the image display device, wherein changes in the treatment instrument orientation change the corresponding region of the treatment path displayed on the image display device.

23. The system of claim 21, further comprising:

means to adjust at least one parameter of power, pulse frequency, pulse amplitude, and duration, thereby adjusting the energy profile of the treatment instrument, wherein the adjustments are reflected on the image display device as changes in a size or shape of the region of the treatment path based on the adjusted parameters.

24. The method of claim 18, wherein the location finding imaging instrument and the treatment instrument are movable independently from one another in three dimensions.

25. A system for visually displaying and treating a location to be treated within a treatment volume in a human or animal body, the system comprising:

a location finding imaging instrument configured to detect the treatment volume and the location to be treated within the treatment volume;

a treatment instrument configured to direct enemy along a treatment path at the location to be treated within the treatment volume;

an image display device; and at least one control unit configured to control the image display device to display the detected treatment volume, the detected location to be treated within the treatment volume, and an enemy level region of the treatment path, wherein the image display device displays the region of the treatment path as an area in a single plane superimposed on the treatment volume and the location to be treated within the treatment volume, wherein the location finding imaging instrument and the treatment instrument are movable independently from one another in three dimensions.

26. The system of claim 25, wherein the treatment instrument is a shock wave instrument, and wherein the region of the treatment path is a projected shock wave energy profile set at a predetermined energy.

27. The system of claim 25, wherein the at least one control unit is configured to process information received from the location finding instrument and the treatment instrument and to communicate signals based on the received information to the image display device, wherein the image display device displays the treatment volume, the location to be treated within the treatment volume, and the region of the treatment path based on the signals from the at least one control unit.

28. The system of claim 27, further comprising:

means for orienting the location finding imaging instrument; and means for orienting the treatment instrument in response to the location to be treated within the treatment volume displayed on the image display device, wherein changes in the treatment instrument orientation change the corresponding region of the treatment path displayed on the image display device.

29. The system of claim 27, further comprising:

means to adjust at least one parameter of power, pulse frequency, pulse amplitude, and duration, thereby adjusting the energy profile of the treatment instrument, wherein the adjustments are reflected on the image display device as changes in a size or shape of the region of the treatment path based on the adjusted parameters.

30. The system of claim 25, further comprising a processor configured to simulate activation of the treatment instrument to determine a simulated region of the treatment path prior to activation of the treatment instrument, wherein the image display device displays the simulated region of the treatment path as the area in a single plane superimposed on the displayed treatment volume and location to be treated within the treatment volume.

31. The system of claim 25, wherein the image display device displays the region of the treatment path as a three dimensional shape superimposed on the displayed treatment volume and location to be treated within the treatment volume.

* * * * *

UNITED STATES PATENT AND TRADEMARK OFFICE
CERTIFICATE OF CORRECTION

PATENT NO. : 7,610,079 B2
APPLICATION NO. : 11/459664
DATED : October 27, 2009
INVENTOR(S) : Werner Schwarze et al.

It is certified that error appears in the above-identified patent and that said Letters Patent is hereby corrected as shown below:

Claim 1, column 7, line 30,

"treatment volume;" should read -- treatment volume, the location finding imaging instrument having an axis of orientation Ai, --

Claim 1, column 7, line 32-34,

"to direct energy along a treatment path in response to the display of the treatment volume and the location to be treated within the treatment volume;" should read -- to direct energy along a treatment path having a centerline directed along an axis At in connection with the display of the treatment volume and the location to be treated within the treatment volume, wherein the treatment instrument is positioned with respect to the location finding imaging instrument such that the axis Ai and the axis At intersect at an angle that is greater than zero degrees; --

Claim 18, column 8, line 67,

"within the treatment volume;" should read -- within the treatment volume, the location finding imaging instrument having an axis of orientation $A_i$; --

Claim 18, column 9, line 3,
"volume;" should read -- volume, the treatment path having a centerline directed along an axis $A_t$, wherein the treatment instrument is positioned with respect to the location finding imaging instrument such that the axis $A_i$ and the axis $A_t$ intersect at an angle that is greater than zero degrees; --

Claim 25, column 9, line 59,

"within the treatment volume;" should read -- within the treatment volume, the location finding imaging instrument having an axis of orientation $A_i$; --

Claim 25, column 10, line 3,

"treatment volume," should read -- treatment volume, the treatment path having a centerline directed along an axis $A_t$, wherein the treatment instrument is positioned with respect to the location finding imaging instrument such that the axis $A_i$ and the axis $A_t$ intersect at an angle that is greater than zero degrees; --

Signed and Sealed this

Twenty-third Day of March, 2010

David J. Kappos
*Director of the United States Patent and Trademark Office*